United States Patent [19]

Coles

[11] 4,191,854
[45] Mar. 4, 1980

[54] TELEPHONE-COUPLED VISUAL ALPHANUMERIC COMMUNICATION DEVICE FOR DEAF PERSONS

[76] Inventor: George A. Coles, 2917 S. Fifth St., Springfield, Ill. 62703

[21] Appl. No.: 867,535

[22] Filed: Jan. 6, 1978

[51] Int. Cl.² .............................................. H04M 11/06
[52] U.S. Cl. .................................... 179/2 R; 179/84 L
[58] Field of Search .................. 179/2 R, 2 A, 2 DP, 179/27 FC, 84 L, 84 VF, 81 C; 340/366 R, 371, 407

[56] References Cited

U.S. PATENT DOCUMENTS

| | | | |
|---|---|---|---|
| 3,582,554 | 6/1971 | Le Blang | 179/84 VF |
| 3,585,303 | 6/1971 | Chieffo | 179/84 L |
| 4,012,599 | 3/1977 | Meyer | 179/2 DP |

Primary Examiner—Bernard Konick
Assistant Examiner—Joseph A. Popek
Attorney, Agent, or Firm—Ralph F. Staubly

[57] ABSTRACT

A portable self-powered electrically conductively isolated device converts alphanumeric electric signals transmitted from a Touch-Tone telephone at a sending station to visual signals at a receiving telephone station. A magnetic pickup is attached to the activated receiving telephone, as by a suction cup, and feeds two-frequency Touch-Tone signals to tuned detectors which energize two overlapped parallel-busbar grids interconnected at their crossover points by panel-displayed light-emitting diodes. By code the touch-sent signals are converted to visually received signals; for example, on pushbutton 5 one touch means "J", two touches "K" and three touches "L".

3 Claims, 2 Drawing Figures

TELEPHONE-COUPLED VISUAL ALPHANUMERIC COMMUNICATION DEVICE FOR DEAF PERSONS

BACKGROUND AND OBJECTS OF THE INVENTION

It is known to employ Touch-Tone-telephone-transmitted signals in communication systems for the deaf (e.g. the patent to Meyer U.S. Pat. No. 4,012,599, Mar. 15, 1977). But most known systems are complicated and expensive to make and maintain. It is accordingly the object of the present invention to provide a very simple, inexpensive, yet highly effective Touch-Tone-telephone-coupled communication device for deaf persons.

Figure 1:
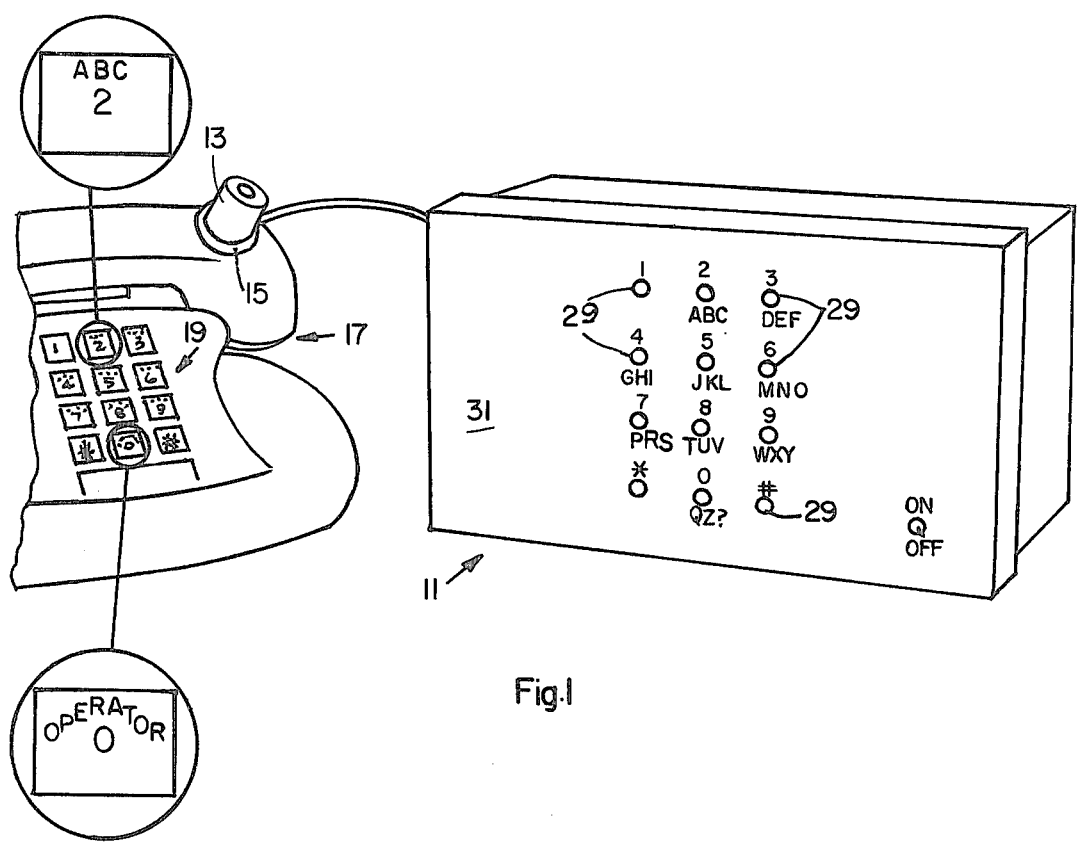
FIG. 1 is a front elevational perspective view of a preferred embodiment of the receiver shown connected to an out-of-service telephone.

With reference now to the drawing, the numeral 11 generally designates a preferred embodiment of the receiver, which includes a magnetic pickup 13 having a suction-cup 15 for quick and easy attachment to the appropriate part of a telephone 17. The telephone 17 has a conventional Touch-Tone keyboard 19 and electronic circuitry (not shown) of known construction for transmitting two-frequency dialing signals.

After the dialing operation has established communication with a deaf person at a receiving station, the Touch-Tone buttons can continue to be actuated to send a series of two-frequency signals for conversion by a code to visible signals on the receiver 11.

Figure 2:
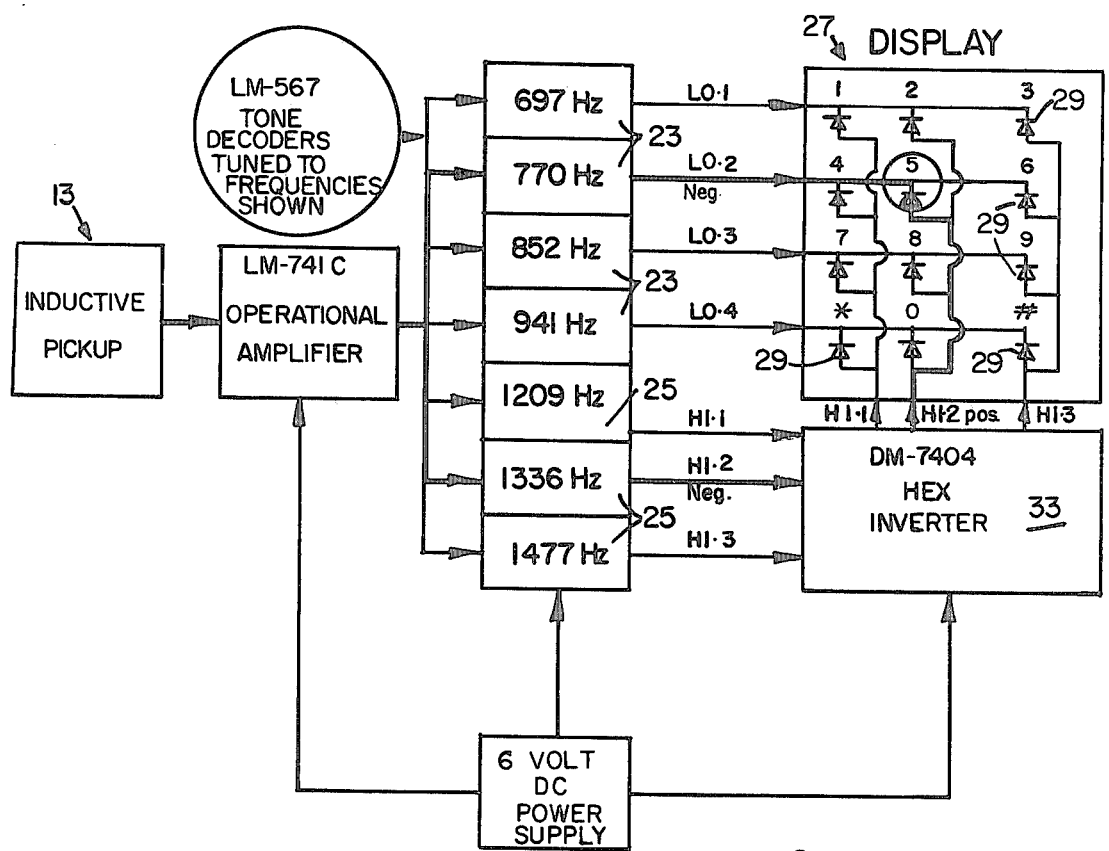
FIG. 2 is a schematic block diagram of the receiver of FIG. 1.

The inductive pickup 13 is coupled by an amplifier LM-741C (FIG. 2) to four low-frequency tuned detectors (decoders) 23 and to three high-frequency tuned detectors 25, which detectors 23 and 25 are tuned to the conventional Touch-Tone frequencies shown in FIG. 2. The detectors thus transmit only one low-frequency and only one high-frequency pulse to the display panel 27 for each push-button touch.

The display panel 27 is shown as having twelve light-emitting diodes (LEDs) 29 exposed in apertures in a face panel 31. The LED arrangement pattern corresponds to the pattern of the Touch-Tone buttons and presents the same numerals and letters.

The cathodes of the LEDs in each horizontal row are connected to the output lead from one low-frequency detector 23. The anodes of the LEDs in each vertical row are connected to the output lead from one high-frequency detector 25. Because the outputs from all of the detectors would be of the same polarity, it is necessary to invert the polarity of either the low- or the high-frequency signals by an inverter unit 33 (of known construction).

For example, when the "5" (or "JKL") button is depressed, the 5 LED on the panel 31 will glow as long as the 5 button is held depressed, thus sending either a numeric ("5") or an alpha ("J") signal depending on the code status (as explained hereinafter). If letters are being sent, two button touches would mean "K", and three would mean "L". The heavy connecting leadlines in FIG. 2 show the current flow which energizes LED 5 when Touch-Tone button 5 is pressed.

For an example of the type of codes that could be employed, for ten-key or twelve-key systems, A would require one touch on key 2, B two touches on key 2, and C three touches on key 2. Thus A-2, B-22, C-222; D-3, E-33, F-333; J-5, K-55, L-555; W-9, X-99, Y-999; Z-00; ?-000. For ten or twelve keys, "1" could indicate the end of a word, "11" the end of a sentence, and "111" the end of a message. With ten keys, "0000" could mean "numbers follow", and "1111" mean "end of numbers". With twelve keys, "#" could mean "numbers to follow", "##" mean "end of numbers", "*" mean "yes", and "**" mean "no". Thus the word "EXAMPLE" would be sent as follows:

| 33 | 99 | 2 | 6 | 7 | 555 | 33 | 1 |
|----|----|----|----|----|-----|----|----|
| E | X | A | M | P | L | E | . |

The invention having been described, what is claimed as being patentable is:

1. A receiver for converting alphanumeric two-frequency electrical signals transmitted from a push-button telephone to visible signals at a message-receiving station, said receiver comprising: an inductive pickup easily removably attachable to a telephone constituting part of said message-receiving station, an amplifier having its input connected to said inductive pickup for amplifying received electrical signals, a bank of differently tuned high-frequency detectors, a bank of differently tuned low-frequency detectors, said amplifier having its output connected to the input of said detectors, a display having a plurality of row conductors and a plurality of column conductors, a plurality of cross-points each formed by the intersection of a row conductor and a column conductor, a plurality of light-emitting diodes each connected between a row conductor and a column conductor at each cross-point, each high-frequency detector being connected to one of said column conductors and each low-frequency detector being connected to one of said row conductors, an inverter unit inserted between either the high-frequency or the low-frequency bank of detectors and the its connected conductors, and a power supply for said receiver, said receiver being electrically conductively isolated from the telephones at the sending and receiving stations.

2. A receiver according to claim 1 wherein said inductive pickup includes means for quick and easy attachment to and detachment from said receiving-station telephone at an appropriate location thereon.

3. A receiver according to claim 2 wherein said means for quick and easy attachment and detachment comprises a suction cup.

* * * * *